(12) United States Patent
Hollister et al.

(10) Patent No.: US 7,174,282 B2
(45) Date of Patent: Feb. 6, 2007

(54) DESIGN METHODOLOGY FOR TISSUE ENGINEERING SCAFFOLDS AND BIOMATERIAL IMPLANTS

(76) Inventors: Scott J Hollister, 2105 Churchill Dr., Ann Arbor, MI (US) 48103; Gabriel Tien-Min Chu, 2609 Mead Ct., Ann Arbor, MI (US) 48105; Juan M Taboas, 436 Kellogg St., Apt. 125, Ann Arbor, MI (US) 48105

(*) Notice: Subject to any disclaimer, the term of this patent is extended or adjusted under 35 U.S.C. 154(b) by 826 days.

(21) Appl. No.: 10/178,419

(22) Filed: Jun. 24, 2002

(65) Prior Publication Data

US 2003/0069718 A1 Apr. 10, 2003

Related U.S. Application Data

(60) Provisional application No. 60/300,354, filed on Jun. 22, 2001.

(51) Int. Cl.
G06F 17/10 (2006.01)

(52) U.S. Cl. .................. 703/2; 703/1; 703/11; 382/128; 424/423

(58) Field of Classification Search .................. 703/1, 703/2, 11; 700/197; 424/93.1, 93.7, 422, 424/423, 426, 443; 382/128
See application file for complete search history.

(56) References Cited

U.S. PATENT DOCUMENTS

| 5,227,979 | A | 7/1993 | Fukuhira et al. ............ 700/197 |
|---|---|---|---|
| 5,680,317 | A | 10/1997 | Watanabe ...................... 703/1 |
| 5,762,125 | A | 6/1998 | Mastrotio .................... 164/4.1 |
| 6,013,853 | A | 1/2000 | Athanasiou et al. ........ 424/423 |
| 6,143,293 | A | 11/2000 | Weiss et al. ............... 424/93.7 |
| 6,192,327 | B1 | 2/2001 | Nishiyama et al. ............ 703/2 |
| 6,233,499 | B1 | 5/2001 | Matsumoto .................. 700/197 |
| 6,306,424 | B1 * | 10/2001 | Vyakarnam et al. ........ 424/426 |
| 6,365,149 | B2 * | 4/2002 | Vyakarnam et al. ....... 424/93.1 |
| 6,534,084 | B1 * | 3/2003 | Vyakarnam et al. ........ 424/443 |
| 2001/0033857 | A1 * | 10/2001 | Vyakarnam et al. ........ 424/443 |
| 2002/0182241 | A1 * | 12/2002 | Borenstein et al. ......... 424/422 |

OTHER PUBLICATIONS

Ku et al., D.N. Development of a New Scaffold for Tissue Engineering, IEEE, Proceedings of the First Joint BMES/EMBS Conference, Oct. 1999, p. 120.*

Sterkman et al., L.G.W. The Frontier of Substitution Medicine: Integrating Biomaterials and Tissue Engineering, IEEE, Engineering in Medicine and Biology Mahazine, vol. 19, No. 3, May/Jun. 2000, pp. 115-117.*

(Continued)

Primary Examiner—Russell Frejd
(74) Attorney, Agent, or Firm—Harness, Dickey & Pierce, P.L.C.

(57) ABSTRACT

A design methodology is provided for creating biomaterial scaffolds optimized for in vivo function with any 3D anatomic shape. The method creates all designs using voxel based design techniques. It also provides for optimization of implant and scaffold microstructure to best match functional and biofactor delivery (including cells, genes and proteins) requirements. The voxel based design techniques readily allow combination of any scaffold or implant microstructure database with any complex 3D anatomic shape created by CT or MRI scanners. These designs can be readily converted to formats for layered manufacturing or casting.

47 Claims, 5 Drawing Sheets

OTHER PUBLICATIONS

Brey et al., Tissue Engineering Applied to Reconstructive Surgery, IEEE, Engineering in Medicine and Biology Magazine, vol. 19, No. 5, Sep./Oct. 2000, pp. 122-125.*

Vozzi et al., G. Microsyringe Based Fabrication of High Resolution Organic Structures for Bioengineering Applications, IEEE, 1st Annual Int. Conference on Microtechnologies in Medicine and Biology, Oct. 2000, pp. 141-144.*

Gresh et al., D.L. Weave: A System for Visually Linking 3-D and Statistical Visualizations, Applied to Cardiac Simulation and Measurement Data, Proceedings of the Conference on Visualization '00, Oct. 2000, pp. 489-495.*

Zein et al., I. Fused Deposition Modeling of Novel Scaffold Architectures for Tissue Engineering Applications, Biomaterials, vol. 23, No. 4, 2001, pp. 1169-1185.*

Hutmacher, D.W. Scaffolds in Tissue Engineering Bone and Cartilage, Biomaterials, vol. 21, No. 24, Dec. 2000, pp. 2529-2543.*

International Search Report mailed Oct. 2, 2002.

International Search Report mailed Feb. 26, 2003.

* cited by examiner

DESIGN METHODOLOGY FOR TISSUE ENGINEERING SCAFFOLDS AND BIOMATERIAL IMPLANTS

CROSS-REFERENCE TO RELATED APPLICATIONS

This application claims the benefit of U.S. Provisional Application No. 60/300,354, filed Jun. 22, 2001.

FIELD OF THE INVENTION

The present invention relates to biomaterial scaffolds and, more particularly, to a design methodology for tissue engineering scaffolds, biomaterial implants, gene therapy delivery systems, in vitro tissue testing systems and bioreactors, and drug delivery and testing systems.

BACKGROUND OF THE INVENTION

Biomaterial scaffolds for tissue engineering perform three primary functions. The first is to provide a temporary function (stiffness, strength, diffusion, and permeability) in tissue defects. The second is to provide a sufficient connected porosity to enhance biofactor delivery, cell migration and regeneration of connected tissue. The third requirement is to guide tissue regeneration into an anatomic shape.

Unfortunately, the first two functions present conflicting design requirements. That is, increasing connected porosity to enhance cell migration and tissue regeneration decreases mechanical stiffness and strength. Conversely, decreasing porosity increases mechanical stiffness and strength but impedes cell migration and tissue regeneration.

Creating biomaterial scaffolds with internal porous architectures that best satisfy the need for function and connected porosity requires balancing these two competing needs. Prior art approaches to this problem can be divided into two distinct areas. The first area concerns itself with design. The second area concerns itself with fabrication.

A first design approach, tailors microstructures to match specific elastic properties. Unfortunately, this design approach fails to provide the ability to create optimal microstructures in an anatomical shape. Also, this design approach fails to provide for the simultaneous design of a scaffold material property and the design of tissue structures in the scaffold pore space. Finally, this design approach fails to allow for the design of both scaffold material and scaffold architecture.

A second design approach uses CT data to create customized bone implants that can be manufactured using solid free form fabrication techniques. Unfortunately, this design approach does not include any specific design method to create the interior of the implant. Also, this design approach does not provide for optimized scaffold architectures with exterior anatomical shapes. Finally, this approach relies upon computer aided design (CAD) techniques which are based on computational geometry entities like surfaces and splines that are not closely related to arbitrary, complex, anatomical geometries and cannot readily use the clinical imaging data that is the basis of creating an anatomically shape scaffold.

The fabrication approach uses solid free form fabrication techniques for tissue engineering scaffolds. This technique is based on the ability to directly manufacture tissue engineering scaffolds using solid free form fabrication. In addition, this technique relies upon computer assisted design or computer aided design to create the scaffold interior design and uses CT scans to provide a template for the anatomic shape.

Unfortunately, the fabrication approach does not have the capability to optimize scaffold architecture and materials to attain natural tissue properties. Also, the fabrication approach relies upon CAD techniques which rely on the use of computational geometry entities like surfaces and splines to represent geometry. Although image data can be converted into geometric data, this does not allow for the design of arbitrary complex geometry. Furthermore, CAD techniques do not allow for the combination of optimal scaffold architectures within many anatomical shapes. Finally, the fabrication approach does not allow for the creation of designs by casting.

SUMMARY OF THE INVENTION

The present invention creates anatomically shaped scaffold architectures with heterogeneous material properties, including interconnecting pores. The pore structure and scaffold material are optimized such that both the scaffold itself and the eventual regenerating tissue match the physical properties of natural tissue while at the same time the scaffold structure is maintained with a fixed lower bound on porosity and permeability. In addition, the pore architecture is simultaneously optimized such that tissue growing into the pores will maintain desired physical properties.

The methodology of the present invention combines image-based design of pore structures with homogenization theory to compute effective physical property dependence on material microstructure. Optimization techniques are then used to compute the optimal pore geometry. The final optimized scaffold geometry voxel topology is then combined with a voxel data set describing the anatomic scaffold shape. Density variations within the anatomic scaffold voxel database are used as a map to guide where different optimized scaffold voxel topologies are substituted. The final voxel representation of the anatomically shaped scaffold with optimized interior architecture is converted automatically into either a surface or wire frame representation for fabrication by way of solid free form fabrication or casting.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENT

The following description of the preferred embodiment is merely exemplary in nature and is in no way intended to limit the invention, its application, or uses.

The present invention is generally directed towards a method approach for designing tissue engineering scaffolds, biomaterial implants, drug delivery systems, gene delivery systems and in vitro tissue testing systems that can be heterogeneously distributed to match any anatomic shape and can be fabricated using solid free form fabrication techniques. This invention incorporates image-based design techniques, homogenization theory, mathematical optimization algorithms, marching cubes and marching squares algorithms to convert image based design data to surface or wire frame geometry, and solid free form fabrication.

Figure 1:
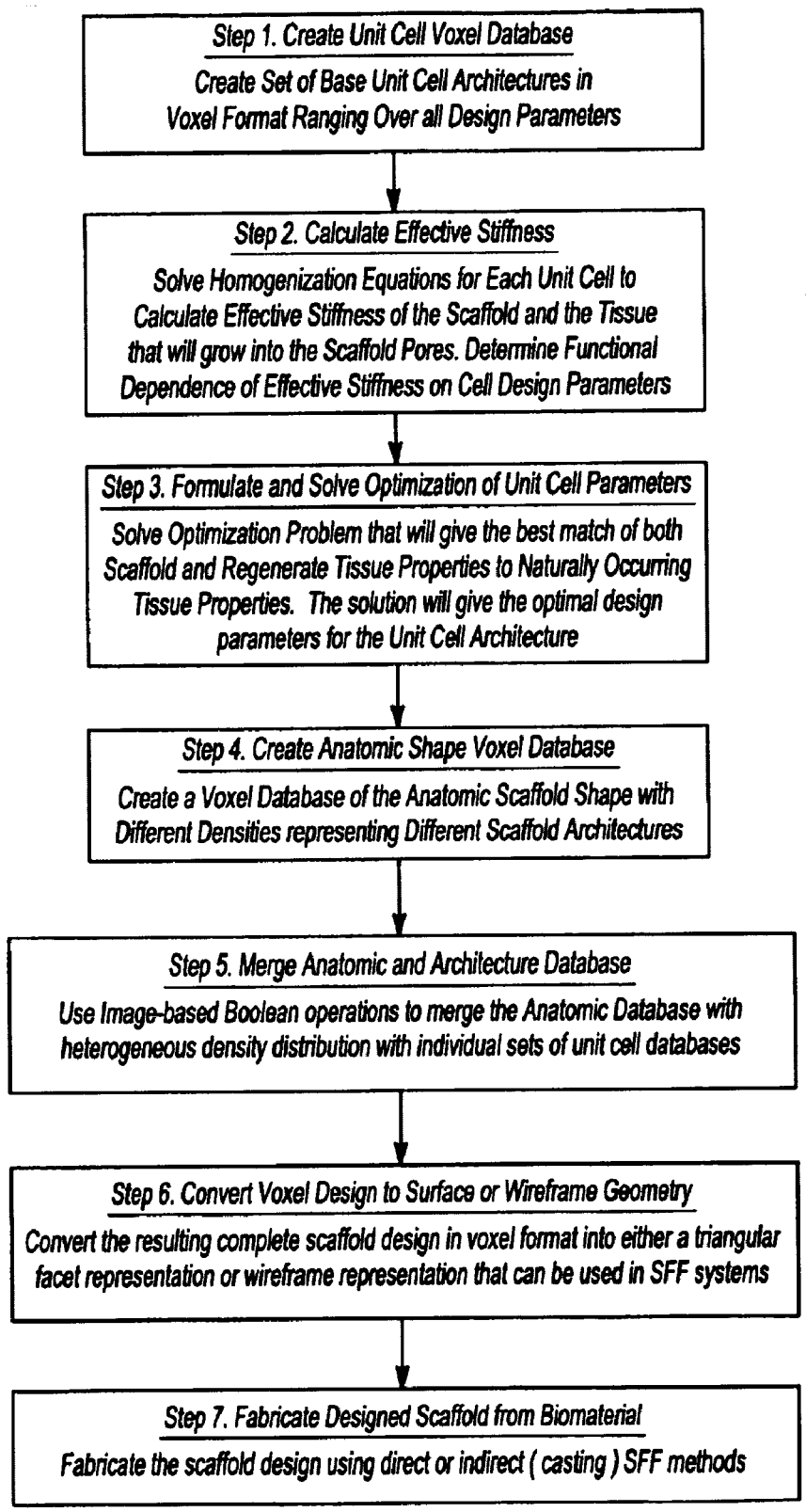
FIG. 1 is a flowchart illustrating the steps for designing scaffolds with specific anatomic shape optimized to match natural tissue properties based on a unit cell architecture in accordance with the teachings of the present invention.

The steps for performing the scaffold optimization of the present invention are shown in FIG. 1. In step 1, the methodology creates unit cell voxel databases. That is, a set of base unit cell architectures are created in voxel format ranging over all design parameters. In step 2, the method calculates effective physical properties. That is, the method solves homogenization equations for each unit cell to calculate effective physical property of the scaffold and the tissue that will grow in to the scaffold pores. The method can also determine functional dependence of effective stiffness, permeability, and porosity on cell design parameters.

In step 3, the method formulates and solves optimization algorithms of unit cell parameters. That is, the method solves the optimization problem that will find the best match of both scaffold and regenerate tissue properties to naturally occurring tissue properties. The solution gives the optimal design parameters for the unit cell architecture. In step 4, the method creates an anatomic shape voxel database. That is, the method creates a voxel database of the anatomic scaffold shape with different densities representing different scaffold architectures.

In step 5, the method merges the anatomic and architecture data base. That is, the method uses image-based Boolean operations to merge the anatomic data base with net erogeneous density distribution with individual sets of unit cell databases. In step 6, the method converts the voxel design to a surface or wire frame geometry. That is, the method converts the resulting complete scaffold design in voxel format to either a triangular facet representation or a wire frame representation that can be used in solid free form systems.

In step 7, the method fabricates the design scaffold from biomaterial. That is, the method fabricates the scaffold design using direct or indirect (casting) solid free form techniques. The methodology steps will now be individually described in greater detail.

Step 1: Create Unit Cell Voxel Databases

The first step in generating the optimal scaffold design is to generate a connected porous unit cell structure. This unit cell structure may be repeated periodically to create a porous architecture. The unit cell pore geometry may be characterized using a limited number of parameters.

Figure 2:
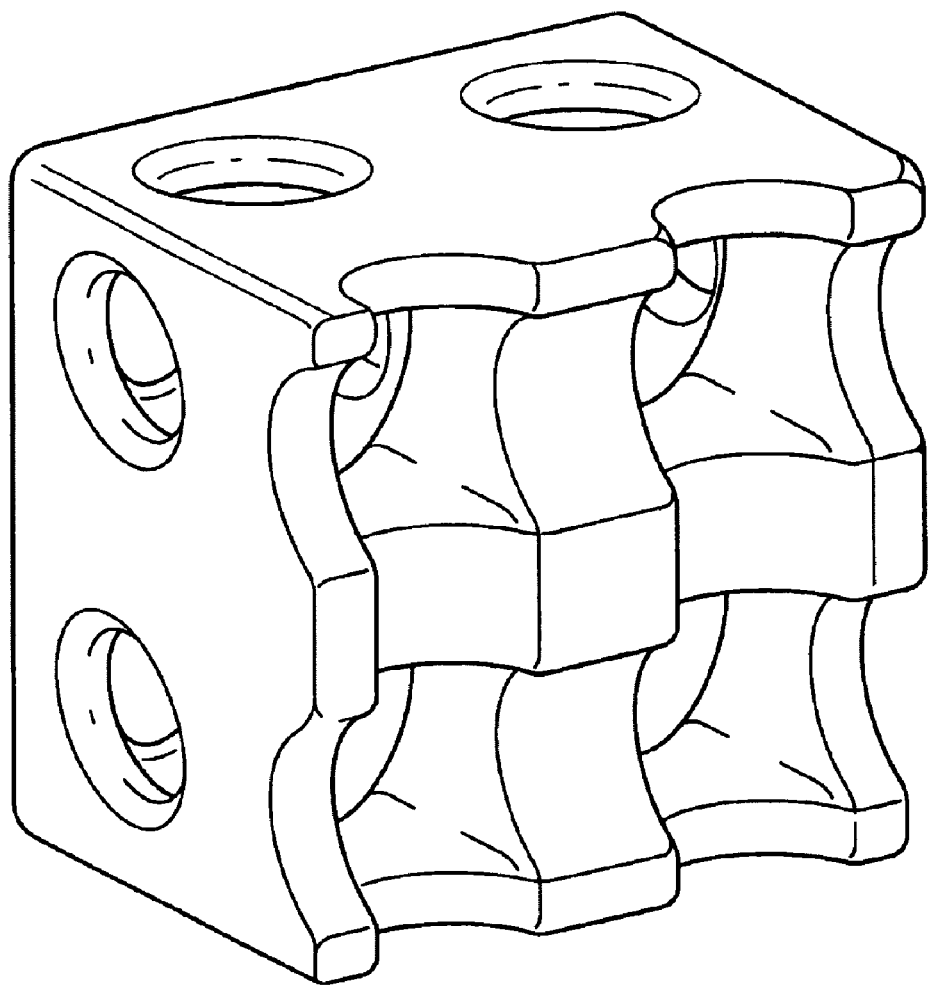
FIG. 2 is a perspective view of a typical porous unit cell structure used for designing the scaffold internal architecture in accordance with the present invention.

For instance, as shown in FIG. 2, if connected cylinders are assumed as the base unit cell structure, the design may be characterized by the three cylinder diameters. The unit cell voxel database may be created in numerous ways, two of which are to 1) generate a geometric architecture by categorizing voxels as inside or outside a structure depending on whether the voxel location satisfies the equation for a specific geometry (FIG. 2) or 2) creating periodically repeating biomimetic structures created from existing tissue architecture.

Step 2: Compute Effective Physical Property-Architecture Dependence Using Homogenization Theory.

The next step is to compute the effective physical property of the base unit cell structure. This is done using a finite element implementation of representative volume element theory such as homogenization. The physical properties of the scaffold may include mechanical stiffness, diffusion, permeability and/or thermal conductivity. All of the formulations below are geared to mechanical stiffness. In homogenization theory, the following weak form of local equilibrium equations are solved:

$$\int_{V_{unit\ cell}} \{\hat{\varepsilon}\}^T [C]\{\varepsilon\}^k dV_{unit\ cell} = \int_{V_{unit\ cell}} \{\hat{\varepsilon}\}^T \{C\}^k dV_{unit\ cell} \qquad (1)$$

where $[C]$ is the base scaffold material stiffness, $\{\}^k$ is a characteristic strain distribution under the $k^{th}$ column of the stiffness matrix $\{C\}^k$. The index k ranges from 1–6 to represent three normal strain states and three shear strain states. $V_{unit\ cell}$ is the unit cell structure volume and $\{\hat{\varepsilon}\}$ is a virtual strain.

Solving equation 1 allows the direct calculation of the effective scaffold stiffness $[C]_{scaf}^{eff}$ and the effective regenerate tissue stiffness $[C]_{tissue}^{eff}$ as:

$$[C]_{scaf}^{eff} = \int_{V_{unit\ cell}} [C]_{scaf} [M]_{scaf} dV_{unit\ cell};$$

$$[M]_{scaf} = [I] - \lfloor \{\epsilon\}^1 \{\epsilon\}^2 \{\epsilon\}^3 \{\epsilon\}^4 \{\epsilon\}^5 \{\epsilon\}^6 \rfloor_{scaf}$$

$$[C]_{tissue}^{eff} = \int_{V_{unit\ cell}} [C]_{tissue} [M]_{tissue} dV_{unit\ cell};$$

$$[M]_{tissue} = [I] - \lfloor \{\epsilon\}^1 \{\epsilon\}^2 \{\epsilon\}^3 \{\epsilon\}^4 \{\epsilon\}^5 \{\epsilon\}^6 \rfloor_{tissue} \qquad (2)$$

where $[C]_{scaf}^{eff}$ is the effective stiffness of the scaffold alone and $[C]_{tissue}^{eff}$ is the effective stiffness of the regenerate tissue that grows into the scaffold pores. $[C]_{scaf}$ and $[C]_{tissue}$ are the base mechanical properties of the scaffold and regenerate tissue, respectively. $[M]_{scaf}$ is a matrix that represents the effective of scaffold architecture on scaffold effective mechanical properties. Likewise, $[M]_{tissue}$ represents the effective of scaffold architecture on regenerate tissue effective mechanical properties.

The quantities $[M]_{scaf}$ and $[M]_{tissue}$ may both be integrated over the volume of each structure phase to give an averaged matrix as follows:

$$[\overline{M}]_{scaf} = \frac{1}{|V_{unitcell}|} \int_{V_{scaf}} [M]_{scaf} dV_{scaf} \quad (3)$$

Likewise, the same may be done for the regenerate tissue matrix:

$$[\overline{M}]_{tissue} = \frac{1}{|V_{unitcell}|} \int_{V_{tissue}} [M]_{tissue} dV_{tissue} \quad (4)$$

If the structure has one dominantly stiff phase, the relationship between the effective scaffold stiffness, the base scaffold stiffness and the scaffold porous architecture may be approximated as:

$$[C]_{scaf}^{eff} \approx [C]_{scaf} [\overline{M}]_{scaf} \quad (5)$$

where $[C]_{scaf}^{eff}$ is the effective scaffold stiffness, $[C]_{scaf}$ is the base scaffold stiffness, and $[\overline{M}]_{scaf}$ is a measure of the scaffold architecture, called the global structure matrix.

Similarly, the relationship between the effective regenerate tissue stiffness, the base regenerate tissue stiffness and the regenerate tissue architecture may be approximated as:

$$[C]_{tissue}^{eff} \approx [C]_{tissue} [\overline{M}]_{tissue} \quad (6)$$

where $[C]_{tissue}^{eff}$ is the effective scaffold stiffness, $[C]_{tissue}$ is the base scaffold stiffness, and $[\overline{M}]_{tissue}$ is a measure in this case of the regenerate tissue architecture.

Equations (5) and (6) are critical to the optimization scheme based in a set of unit cell structures with similar topology because they show that it is possible to compute the entire range of values for $[M]_{scaf}$ and $[M]_{tissue}$, and then fit these values to a known function without having to recalculate them each time the architecture is changed. Specifically, $[M]_{scaf}$ and $[M]_{tissue}$ will be pre-computed and stored as a direct function of the unit cell design parameters.

For example, the intersecting orthogonal cylinder design may be characterized by three design parameters being the three cylinder diameters. The relationship between $[M]_{scaf}$ and the three cylinder diameters for the unit cell design in FIG. 2 can be fit into a third degree polynomial of the form:

$$[\overline{M}_{ij}(d_1,d_2,d_3)] = a_0 + a_1 d_1 + a_2 d_2 + a_3 d_3 + a_4 d_1^2 + a_5 d_1 d_2 +$$
$$a_6 d_1 d_3 + a_7 d_2^2 + a_8 d_2 d_3 + a_9 d_3^2 + a_{10} d_1^3 a_{11} d_1^2 d_2 +$$
$$a_{12} d_1^2 d_3 + a_{13} d_1 d_2^2 + a_{13} d_1 d_2 d_3 + a_{14} d_1 d_3^2 + a_{15} d_2^3 +$$
$$a_{16} d_2^2 d_3 + a_{17} d_2 d_3^2 + a_{18} d_3^3 \quad (7)$$

Note that the coefficients $a^0$–$a^{19}$ are computed for each of the 36 elements of the 6×6 matrix $\overline{M}$ Equations 5 and 6 may now be written in the following functional forms $$[C]_{scaf}^{eff} \approx [C(E_1,E_2,E_3,G_{12},G_{13},G_{23},v_{12},v_{13},v_{23},)]_{scaf}[\overline{M}(d_1,d_2,d_3,)]_{scaf}$$

$$[C]_{tissue}^{eff} \approx [C]_{tissue}[\overline{M}(d_1,d_2,d_3)]_{tissue} \quad (8)$$

Equation 8 shows that we can simultaneously design the scaffold and the regenerate tissue effective stiffness by controlling the stiffness of the base scaffold material, $[C(E_1,E_2,E_3,G_{12},G_{23},v_{12},v_{13},v_{23},)]_{scaf}$, the scaffold porous architecture $[\overline{M}(d_1,d_2,d_3)]_{scaf}$ and the pore structure into which the tissue grows $[\overline{M}(d_1,d_2,d_3)]_{tissue}$. Note that if permeability and/or electrical conductivity properties are to be optimized, the relationship of permeability and conductivity to microstructure properties can be written as:

$$[K]_{scaf}^{eff} \approx [K(K_1,K_2,K_3)]_{scaf}[\overline{M}(d_1,d_2,d_3,)]_{scaf}$$

$$[K]_{tissue}^{eff} \approx [K]_{tissue}[\overline{M}(d_1,d_2,d_3)]_{tissue}$$

where again $[\overline{M}(d_1,d_2,d_3)]_{scaf}$ represents the scaffold architecture, $[\overline{M}(d_1,d_2,d_3)]_{tissue}$ represents the regenerate tissue architecture, $[K]_{scaf}^{eff}$ represents the effective scaffold permeability or conductivity, $[K]_{tissue}^{eff}$ represents the effective tissue permeability or conductivity, $[K]_{scaf}$ is the base scaffold permeability or conductivity and $[K]_{tissue}$ is the base tissue permeability or conductivity.

Thus, the use of unit cell based periodic architecture and homogenization theory has allowed the development of an explicit functional dependence of scaffold effective stiffness and regenerate tissue effective stiffness on scaffold base material and scaffold porous architecture. Note that the regenerate tissue base stiffness cannot be designed so it does not enter the equation.

Step 3: Formulate and Solve Optimization of Unit Cell Parameters

Equation 8 provides the basis for optimizing scaffold base material properties and architecture such that both scaffold effective stiffness and regenerate tissue stiffness match desired natural tissue properties. It may also be important to place a constraint on the scaffold porosity and/or permeability. Functional dependence of both porosity and permeability can be computed using homogenization theory and expressed in a functional form like equation 7.

Accounting for scaffold stiffness, regenerate tissue effective stiffness, scaffold porosity and scaffold permeability allows for a very general scaffold design. The advantage of creating explicit functional representations like equation 7 is that general mathematical programming algorithms available in numerical packages like MATLAB™ can be applied to solve very general optimization problems. A typical optimization formulation where the objective is to have both effective scaffold stiffness and regenerate tissue stiffness match natural tissues stiffness with a constraint on scaffold porosity is given below:

$$E^{scaffold}\text{Min}, d_1, d_2, d_3 \sum_{i=1}^{n} \left( \frac{C_i^{natural\ tissue\ eff} - C_i^{regen\ tissue\ eff}}{C_i^{natural\ tissue\ eff}} \right)^2 + \quad (9)$$

$$\sum_{i=1}^{n} \left( \frac{C_i^{natural\ tissue\ eff} - C_i^{scaffold\ eff}}{C_i^{natural\ tissue\ eff}} \right)^2 \text{ where } i = 1 \text{ to } 9$$

Subject to:
$d_1, d_2, d_3 \leq 900$ microns
$d_1, d_2, d_3 \geq 300$ microns
$V_{pore}/V_{total} \geq \%$ Porosity
$E^{scaffold} \geq E_{min}$
$E^{scaffold} \geq E_{max}$ where Min stands for Minimize, $E^{scaffold}$ is the Young's modulus of the scaffold base material under the assumption of isotropy, and $d_1, d_2, d_3$ are the diameters of the cylindrical pores for the unit cell shown in FIG. 2. $E^{scaffold}$, $d_1, d_2$ and $d_3$ are all design variables for the scaffold base material and architecture.

In the objective function, $C_i^{regen\ tissue\ eff}$ is the matrix of the effective regenerate tissue elastic properties, $C_i^{scaf\ eff}$ is the matrix of the effective scaffold tissue elastic properties, and $C_i^{natural\ tissue\ eff}$ is the matrix of the desired target effective natural tissue elastic properties. The values $E_{min}$ and $E_{max}$ are the lower and upper bound constraints on the Young's modulus of the scaffold base material. The quantities $V_{pore}$ and $V_{total}$ are the volume of scaffold pores and total scaffold volume respectively. This optimization formulation seeks to match both the scaffold and regenerate tissue effective properties as close to the natural tissue properties while satisfying constraints on the cylinder diameters ($d_1, d_2,$ and $d_3$), the scaffold porosity $$\left(\frac{V_{pore}}{V_{total}}\right),$$

and the minimum and maximum value ($E_{min}, E_{max}$) of the scaffold base material stiffness. Note again that other physical properties like permeability and conductivity may be designed.

A second typical optimization formulation using this approach is:

$$E^{scaffold Max}, d_1, d_2, d_3 \frac{V_{pore}}{V_{total}}$$

Subject to:
$\partial_1 C_i^{bone\ eff} \leq C_i^{tissue\ eff} \leq \alpha_2 C_i^{bone\ eff}$ where i=1 to 9; $\alpha_2 > \alpha_1$
$\beta_1 C_i^{bone\ eff} \leq C_i^{scaffold\ eff} \leq \beta_2 C_i^{bone\ eff}$ where i=1 to 9; $\beta_2 > \beta_1$
$d_1, d_2, d_3, \leq 900$ microns
$d_1, d_2, d_3 \geq 300$ microns
$E^{scaffold} \geq E_{min}$
$E^{scaffold} \leq E_{max}$ where again $E^{scaffold}$ is the Young's modulus of the scaffold base material under the assumption of isotrophy, $d_1 d_2 d_3$ are the diameters of the cylindrical pores for the unit cell shown in FIG. 2, $C_i^{regen\ tissue\ eff}$ is the matrix of the effective regenerate tissue elastic properties, $C_i^{scaf\ eff}$ is the matrix of the effective scaffold tissue elastic properties, $C_i^{natural\ tissue\ eff}$ is the matrix of the desired target effective natural tissue elastic properties, $E_{min}$ and $E_{max}$ are the lower and upper bound constraints on the Young's modulus of the scaffold base material, and $V_{pore}$ and $V_{total}$ are the volume of scaffold pores and total scaffold volume respectively.

In the equation, $\alpha_1, \alpha_2, \beta_1,$ and $\beta_2$ are scaling factors used to bound the scaffold and regenerate tissue effective stiffness. The new quantities $\alpha_1, \alpha_2, \beta_1$ and $\beta_2$ are weighting factors on the stiffness terms that modify how tightly the designed stiffness must match the target stiffness as a constraint. This optimization formulation seeks to design a scaffold with the maximum porosity possible that still matches the desired stiffness and base scaffold material properties within defined constraints.

A third possible optimization formulation can include permeability of the scaffold as a constraint. Permeability is important in a scaffold for two reasons. First, to load biofactors initially into the scaffolds, a high permeability is needed to ensure flow of the biofactors through the scaffold architecture. Second, in vivo, high permeability is associated with the ability of cells to migrate into the scaffold.

A typical optimization formulation with a constraint on scaffold permeability would have the form:

$$E^{scaffold Min}, d_1, d_2, d_3 \sum_{i=1}^{n} \left(\frac{C_i^{natural\ tissue\ eff} - C_i^{regen\ tissue\ eff}}{C_i^{natural\ tissue\ eff}}\right)^2 +$$

$$\sum_{i=1}^{n}\left(\frac{C_i^{natural\ tissue\ eff}}{C_i^{natural\ tissue\ eff}}\right)^2 \text{ where } n = 1 \text{ to } 9$$

Subject to:

$\alpha_1 K_i^{target} \leq K_i^{target} \leq \alpha_2 K_i^{target}$ where $i = 1$ to 3; $\alpha_2 > \alpha_1$    (11)

$d_1, d_2, d_3 \leq 900$ microns $d_1, d_2, d_3 \geq 300$ microns $\frac{V_{pore}}{V_{total}} \geq \%\ Porosity$ $E^{scaffold} \geq E_{min}$ $E^{scaffold} \leq E_{max}$ where all quantities are as defined in equation 9 with the exception of the first line of constraints with $K_i^{t\ arg\ et}$ being the target scaffold permeability and $\alpha_1$ and $\alpha_2$ the weighting factors for the permeability constraint.

Optimization formulations presented in equations 9–11 may be solved using standard mathematical programming algorithms such as those available in MATLAB™ or Numerical Recipes. This allows many different optimization formulations to be solved for any particular design.

In contrast to available topology optimization methods, for which a large finite element problem must be solved at each optimization iteration, the current invention streamlines the process albeit with a more restricted set of available topologies. In other words, the current invention allows a much more rapid solution of the topology optimization problem for a scaffold (with commercially available software) than other topology optimization approaches at the cost of using a more restricted set of topologies.

A typical implementation in MATLAB™ using the $f_{mincon}$ option from the MATLAB™ toolkit (a Sequential Quadratic Programming Algorithm) has the following form:

[x.fval]+fmincon(objective function,x0,[],[],[],[],lb, ub,nonlinear constraint)

where x is a vector of design variables being the scaffold architecture parameters and scaffold material properties, 'objective function' is a MATLAB™ m-file containing the objective function evaluation, x0 is the initial value of the design variables, lb is the lower bound on scaffold material stiffness and scaffold wall thickness, ub is the upper bound on scaffold material stiffness and scaffold wall thickness, and 'nonlinear constraint' is the MATLAB™ constraint file containing the evaluation of the volume fraction constraint or effective stiffness, both of which are nonlinear.

For this study, the three orthogonal Young's moduli for mandibular condyle trabecular bone reported by Teng and Herring were chosen as the target bone properties for the optimization problem. For the stiffness design, the porosity constraint was set a 60%. For the porosity design, the scaling factors were set to 0.9 and 1.1 for both tissue ($\alpha_1, \alpha_2$) and scaffold stiffness ($\beta_1, \beta_2$). This meant that both the scaffold and regenerate tissue effective properties must be between 90% and 110% of the original bone properties. For both design problems, $E_{min}$ was set to 1.5 GPa to represent a lower bound for degradable polymer properties and $E_{max}$ was set to 15 GPa to represent calcium-phosphate ceramic properties. The regenerating tissue was assumed to be isotropic using a value of 5 GPa, an upper bound from experimental results of Guldberg and Hollister.

Step 4: Creating Anatomic Shape Voxel Databases

The fourth step in creating anatomically shaped tissue engineered scaffolds with optimized architecture is to create the anatomic shape in a voxel database of the same form as the optimized internal architecture voxel database. The most direct way to create the anatomic shape voxel database is to image the desired section of a patient's anatomy using either Computed Tomography (CT) or Magnetic Resonance Imaging (MRI) techniques. These techniques automatically create a three-dimensional (3D) voxel database representing the complex anatomic topology by a density distribution within a fixed voxel grid.

The original density distribution within the anatomic database reflect attenuation of a signal through tissues. For the purpose of scaffold design, this density alteration is modified to serve as a marker for the placement of different scaffold architecture designs. Density modification is accomplished either by directly indexing the anatomic array and changing the density for the given indices, or by using Region of Interest tools to select polygon regions on a slice and changing all pixels within the polygon region to a different density.

Step 5: Merge Anatomic and Architecture Databases

Figure 3:
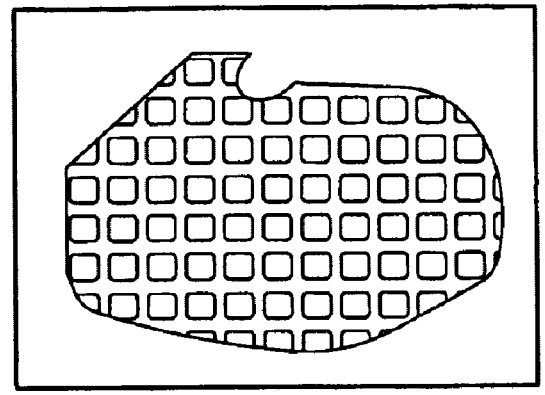
FIG. 3 illustrates an example of a Boolean combination to create a final scaffold voxel topology from an optimized interior porous architecture and an exterior anatomic shape of a mandibular condyle in accordance with the present invention.
Figure 3:
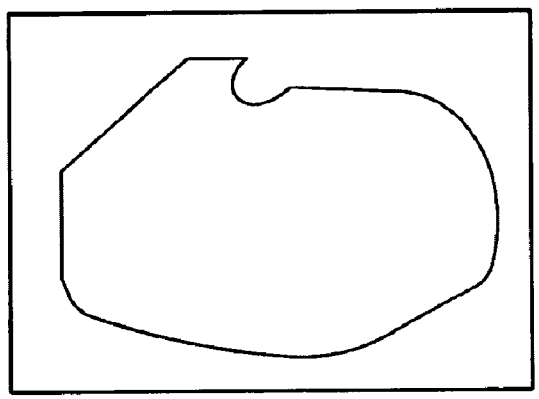
Figure 3:
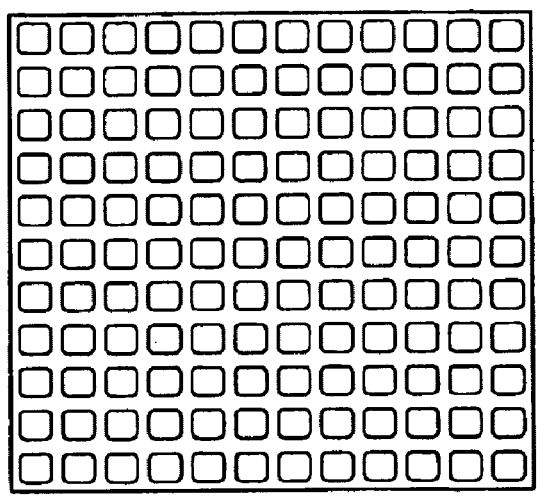

The anatomic voxel data format is the same as the internal architecture database, allowing direct Boolean substitution of a specific internal architecture database directly into a specific location of the anatomic database, using density in the anatomic database as a marker. In other words and referring to FIG. 3, suppose that two specific optimized architectures, denoted as architecture A and architecture B, are created to fill two locations within a given anatomic shape. First, the periodic architecture unit cell database is replicated such that it covers the exact same voxel space as the anatomic voxel database at the same resolution. Following this replication, the array indices for the architecture database exactly match the array indices of anatomic voxel database.

Due to this exact array index matching, the Boolean substitution can be easily done. If the anatomic voxel database is denoted as "anatomy", then the indices of the array where "anatomy" has a given density are substituted with the same indexed voxels from the architecture database that are linked to the specified anatomic density. This produces an optimized internal architecture in the shape of the desired anatomy.

Step 6: Convert Voxel Design to Surface or Wireframe Geometry

Steps 1–6 produce a custom anatomically shaped scaffold with optimally designed interior porous architecture. The design at this point is described completely in a voxel database, with the scaffold topology represented as a density distribution within a fixed voxel grid. To fabricate these designed scaffolds using solid-free form fabrication, computer controlled machining, or other manufacturing techniques typically requires data in either a surface or wireframe geometry.

Specifically for solid free-form fabrication, the surface geometry is used for the .stl file format from 3Dsystems, Inc. For surface representation, a marching cubes algorithm is used to generate an isosurface of triangular facets at a use specified density. These triangular facets are then written in a binary format according to .stl specifications. The generation of triangular facets is automatic, the user need only specify the density level at which the surface is generated from the scaffold design voxel database.

For a wireframe representation, the user specifies a slicing direction and slicing distance. The algorithm then interpolates voxel density from the scaffold design at the specified slicing densities. A contouring algorithm is then used to extract wireframe contours at the specified density. These contours consist of joined polygon lines that are then written directly into either .s1c or .slf format. After creation of either a .stl, slc, or .slf data, the anatomically shaped scaffold with optimized porous architecture can then be built on a variety of solid free-form fabrication systems.

Step 7: Fabricate Designed Scaffold from Biomaterial

The final step in creating the optimized scaffold is to fabricate the optimized design from a biomaterial. This biomaterial may be a ceramic, polymer or metal, so long as it is biocompatible. These optimal designs may be created by a variety of fabrication techniques including solid free-form fabrication and computer controlled milling. Fabrication by solid free-form fabrication includes either direct fabrication from a biomaterial or fabrication of a mold into which a biomaterial may be cast. These solid free-form fabrication techniques include stereolithography (SLA), receive laser sintering (SLS), layered object manufacturing (LOM), direct material deposition (DMD) and thermoplastic printing (Solidscape).

Simulations and Working Models

The above scaffold design procedure has been applied to design a mandibular condyle scaffold with internal architecture optimized to match three elastic Young's moduli of minipig mandibular condyle bone reported by Teng and Herring (1996). The following specific optimization formulation was used:

$$E^{scaffold} \text{ Min}, d_1, d_2, d_3 \sum_{i=1}^{3} \left( \frac{C_i^{natural\ tissue\ eff} - C_i^{regen\ tissue\ eff}}{C_i^{natural\ tissue\ eff}} \right)^2 +$$

$$\sum_{i=1}^{3} \left( \frac{C_i^{natural\ tissue\ eff} - C_i^{scaffold\ eff}}{C_i^{natural\ tissue\ eff}} \right)^2$$

Subject to:
$d_1, d_2, d_3 \leq 900$ microns
$d_1, d_2, d_3 \geq 300$ microns
$V_{pore}/V_{total} \geq 0.60$
$E^{scaffold} \geq 1 \text{GPa}$
$E^{scaffold} \leq 15 \text{GPa}$ where the number of elastic constants to fit in the objective function was set to three (the three orthogonal Young's Moduli from Teng and Herring's data), the porosity bound was set to 60% and the minimum and maximum Scaffold Young's moduli were set to 1 and 15 GPa, respectively, to reflect the Young's modulus of available scaffold material ranging from biopolymers (E-1 CPa) to bioceramics (E=15 GPa).

Figure 4A:
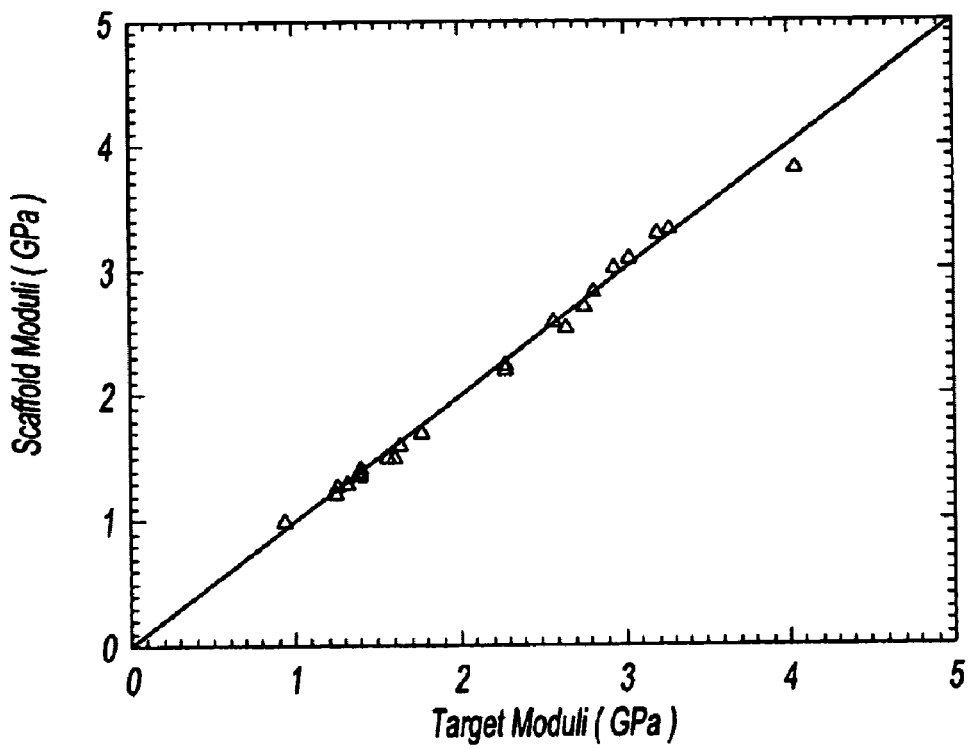
FIG. 4 is a graph illustrating the correlation between scaffold and target bone moduli and regenerate tissue and target bone moduli.
Figure 4B:
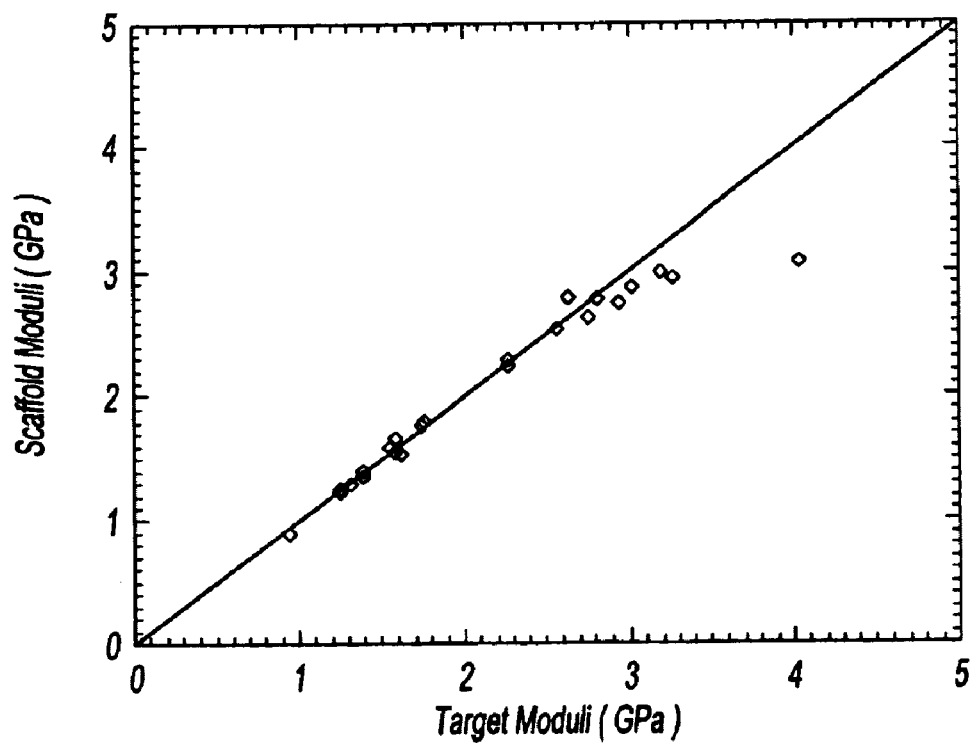

As shown in FIG. 4, the results showed very close agreement between the scaffold moduli and the target bone moduli as well as the regenerate tissue moduli and the target bone moduli.

The $R^2$ values in each case were 0.99 indicating excellent agreement between designed and target properties. The resulting scaffold design parameters and final scaffold porosity are shown in Table 1. Table 1: Results for scaffold base modulus, three pore diameters and scaffold porosity when the scaffold architecture is optimized such that both scaffold and bone regenerate tissue elastic moduli match the target bone moduli from Teng and Herring. Note that all scaffold porosity values match or exceed the minimum value of 0.60 or 60%

| Location | Scaffold Material Modulus (GPa) | Pore 1 Diameter (Microns) | Pore 2 Diameter (Microns) | Pore 3 Diameter (Microns) | Scaffold Porosity |
|---|---|---|---|---|---|
| SupPostMed | 10.7 | .633 | .516 | .777 | .63 |
| SupAntMed | 12.7 | .622 | .470 | .839 | .65 |
| SuPostMid | 9.3 | .591 | .520 | .767 | .71 |
| SupAntMid | 10.0 | .586 | .477 | .808 | .62 |
| SuPostLat | 14.3 | .723 | .512 | .782 | .66 |
| SupAntLat | 15.0 | .715 | .470 | .818 | .67 |
| InfPostMid | 8.7 | .608 | .397 | .810 | .62 |
| InfAntmID | 15.0 | .563 | .536 | .857 | .67 |
| Average | 12.0 | .627 | .489 | .818 | .64 |

The base scaffold moduli vary but typically had values closer to bioceramics. All pore diameters were within the bounds. Finally, all scaffold porosity values met or exceeded the minimum value of 0.6 or 60%.

Taken together, the results from FIG. 4 and Table 1 demonstrate that the current procedure can be used to optimize scaffold architectures such that both the scaffold and regenerate tissue match experimental target properties and the scaffold design parameters and porosity fall within desired limits. In addition, this approach provides for design and selection of the scaffold base material properties.

Figure 5B:
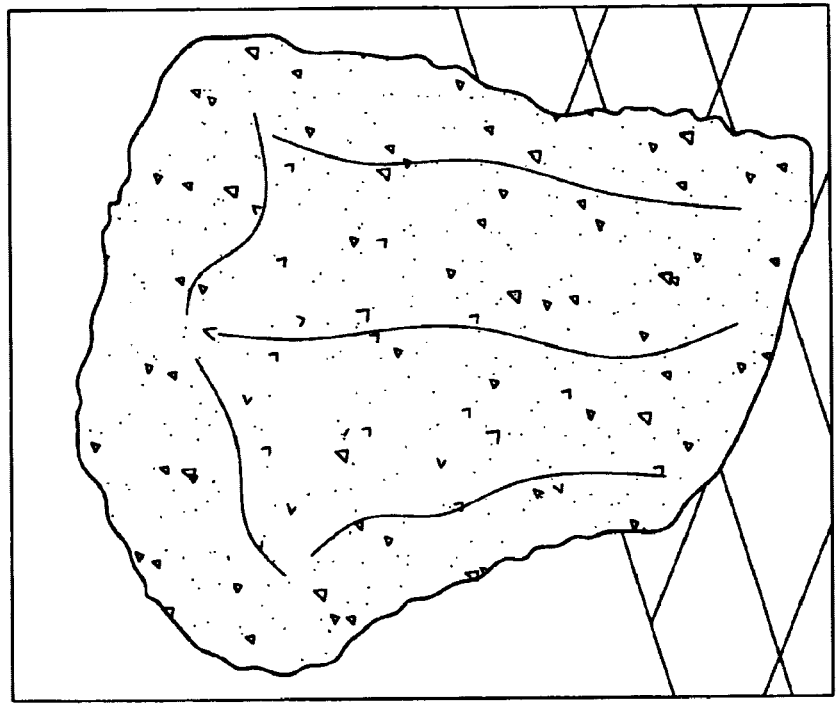
FIG. 5 illustrates the final .stl surface and .slf wire frame representation of optimized scaffold architecture within the shape of a minipig mandibular condyle.
Figure 5A:
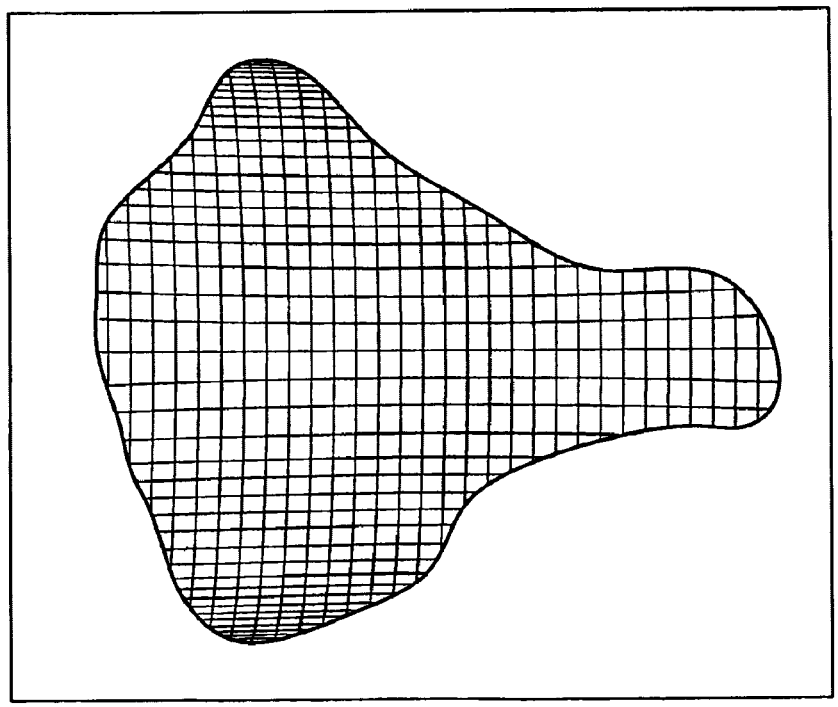

Referring to FIG. 5, one of the optimized architectures was created in the shape of a mandibular condyle to demonstrate the ability to create anatomically shaped scaffolds with optimized interior porous architectures. The final scaffold design was created in both .stl format (FIG. 5a) and .slf format (FIG. 5b). The .slf format (FIG. 6b) has a large number of contours which makes it very difficult to see the details.

The current invention provides the unique ability to optimize scaffold based material properties and scaffold interior architecture for a specific set of topologies, for example, intersecting cylinders. In addition, the invention allows constraints on the range of scaffold material properties, scaffold permeability, and the range of scaffold wall sizes. This type of optimization has not been previously presented for any type of biomaterial scaffold. Also, the invention advantageously uses voxel based topologies to represent both interior scaffold architecture and exterior scaffold shape. This allows two or more architecture databases to be merged into an exterior scaffold shape design using Boolean operations. This invention also uses voxel based techniques to design the initial set of scaffold architectures and homogenization theory to compute the range of effective properties.

The current invention could be applied to design any type of tissue engineering scaffold or biomaterial matrix. These include, but are not limited to:

1. Bone tissue engineering scaffolds;
2. Bone/cartilage tissue engineering scaffolds;
3. Bone/ligament engineering scaffolds;
4. Bone/tendon tissue engineering scaffolds;
5. Blood vessel tissue engineering scaffolds;
6. Liver tissue engineering scaffolds;
7. Abdominal organ scaffolds including kidney, bladder, ureter, etc.
8. Cardiac/skeletal muscle tissue engineering scaffolds;
9. In vitro tissue testing scaffolds including those used in bioreactors
10. Drug delivery systems
11. Delivery systems for gene therapy
12. Joint replacement implants; and
13. Fracture fixation implants.

Potential industries that may find this invention useful include orthopedic and cranial facial device industries, tissue engineering industries, and drug delivery and pharmaceutical industries. Advantageously, the current invention allows the creation of these designs from anatomic images to be completed fairly rapidly, e.g., 1–2 hours. Coupling this with fabrication time, customized scaffolds can be turned around in a 1–2 day time frame.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of designing an implantable member for a patient comprising:
   determining a functional characteristic of a tissue of the patient;
   determining a constraint on the functional characteristic of the tissue;
   creating a first set of databases representing a plurality of microstructure designs for said member in image-based format;
   for each of the plurality of microstructure designs, calculating a functional characteristic of a resultant member incorporating the microstructure designs;
   selecting a desired microstructure design for the member, said selecting step including:
      selecting the desired microstructure design which yields the resultant member most closely matching the functional characteristic of the tissue while satisfying the constraint on the functional characteristic of the tissue;
   creating a second database representing a desired three dimensional shape of the member in image-based format; and
   merging the databases representing the desired microstructure design with the second database to form an image-based design of the member.

2. The method of claim 1 wherein said step of creating the first set of databases further comprises employing a density distribution of the second database as a template for creating the first set of databases.

3. The method of claim 2 wherein the second database represents at least one of an anatomic, exterior and defect shape of a site to be implanted with said member; and
   the first set of databases represent a porous architecture within a three dimensional shape of an external shape of the member.

4. The method of claim 1 wherein said calculating step accounts for regenerate tissue growth into said scaffold.

5. The method of claim 1 wherein said desired microstructure design includes a combination of at least two of said plurality of microstructure designs.

6. The method of claim 1 wherein said desired shape of said member mimics a site in the patient to be implanted with the member.

7. The method of claim 1 wherein:
the functional characteristic of the tissue further comprises at least one of effective linear stiffness, effective nonlinear stiffness, permeability, conductivity, and porosity; and
the constraint on the functional characteristic of the tissue further comprises a threshold tolerance for tissue regeneration.

8. The method of claim 1 wherein:
the functional characteristic of the tissue further comprises vascularization; and
the constraint on the functional characteristic of the tissue further comprises at least one of a threshold effective linear stiffness, effective nonlinear stiffness, permeability, and conductivity.

9. The method of claim 1 wherein said step of calculating a functional characteristic of a resultant member incorporating the microstructure design further comprises accounting for a material degradation profile of a biomaterial forming the member.

10. The method of claim 1 wherein each of said plurality of microstructure designs has a Young's modulus within a pre-selected range.

11. The method of claim 1 wherein said desired microstructure design further comprises a multiple scale microstructure yielding at least one of a desired elasticity, permeability, and conductivity to the member.

12. The method of claim 11 wherein the multiple scale microstructure further comprises local pores and global pores.

13. The method of claim 12 wherein the multiple scale microstructure further comprises micropores having a diameter less than or equal to about 100 μm and macropores having a diameter greater than about 100 μm.

14. The method of claim 1 wherein each of said plurality of microstructure designs has at least one of a minimum level of porosity, conductivity, permeability, modulus, and poisson ratio.

15. The method of claim 1 wherein each of said plurality of microstructure designs has pores with a pre-selected minimum diameter.

16. The method of claim 1 wherein said step of creating the first set of databases further comprises creating the first set of databases in a voxel format.

17. The method of claim 1 further comprising:
converting the image-based design into a fabrication geometry.

18. The method of claim 17 wherein said step of converting the image-based design into the fabrication geometry further comprises converting into at least one of a surface and a wireframe representation.

19. The method of claim 18 further comprising fabricating the member based on the fabrication geometry.

20. The method of claim 19 wherein said step of fabricating the member further comprises a free form fabrication technique.

21. A method of designing a tissue scaffold for replacing native tissue in a patient comprising:
determining a native tissue effective stiffness;
determining a native tissue regeneration requirement;
creating a first set of databases representing a plurality of microstructure designs for said scaffold in image based format;
for each of the plurality of microstructure designs, calculating a scaffold effective stiffness of a resultant scaffold incorporating the microstructure design and a regenerate tissue effective stiffness of regenerate tissue that will grow into the scaffold incorporating the microstructure design;
selecting a desired microstructure design for the scaffold, said selecting step including:
selecting the microstructure design which yields the resultant scaffold most closely matching scaffold effective stiffness and regenerate tissue effective stiffness with native tissue effective stiffness while satisfying the native tissue regeneration requirement;
creating a second database representing a scaffold exterior geometry desired to replace the native tissue in the patient in image based format; and
merging the databases representing the desired microstructure design with the second database into an image-based design of the scaffold.

22. The method of claim 21 further comprising converting the image-based design to a fabrication geometry.

23. The method of claim 22 wherein said fabrication geometry further comprises at least one of surface and wireframe representations.

24. The method of claim 21 wherein said step of creating the first set of databases further comprises employing a density distribution of the second database as a template for creating the first set of databases.

25. The method of claim 24 wherein the second database represents at least one of an anatomic, exterior and defect shape of a site to be replaced with said member; and
the first set of databases represent a porous architecture within a three dimensional shape of an external shape of the member.

26. The method of claim 21 wherein the scaffold geometry further comprises at least one of periodic cells and a biomimetic architecture.

27. The method of claim 21 wherein said step of calculating scaffold effective stiffness of a resultant scaffold and regenerate tissue effective stiffness of tissue that will grow into the scaffold further comprises:
applying a representative volume element theory to each of the plurality of microstructure designs.

28. The method of claim 21 wherein the native tissue regeneration requirement further comprises at least one of a minimum level of porosity to permit tissue ingrowth, a desired pore diameter to permit vascularization, a desired minimum level of permeability, and a desired minimum level of diffusitivity.

29. A method of designing a tissue scaffold for replacing native tissue in a patient comprising:
determining a desired scaffold vascularization;
determining a scaffold stiffness requirement;
creating a first set of databases representing a plurality of microstructure designs for the scaffold in image-based format;
for each of the plurality of microstructure designs, calculating a scaffold vascularization of a resultant scaffold incorporating the microstructure design;
selecting a desired microstructure design for the scaffold, said selecting step including:
selecting the microstructure design which yields the scaffold vascularization most closely matching the desired scaffold vascularization while satisfying the scaffold stiffness requirement;
creating a second database representing a site to be replaced with the scaffold in imaged-based format; and merging the databases representing the desired microstructure design with the second database to yield an image-based design of the scaffold.

30. The method of claim 29 further comprising converting the image-based design to a fabrication geometry.

31. The method of claim 30 wherein said fabrication geometry further comprises at least one of surface and wireframe representations.

32. The method of claim 29 wherein said step of calculating a scaffold vascularization of a resultant scaffold incorporating the microstructure design further comprises:
applying a representative volume element theory to each of the plurality of microstructure designs.

33. A method of designing a drug/gene delivery scaffold for implanting in a patient comprising:
determining a desired functional characteristic of the drug/gene delivery scaffold;
determining a constraint on the functional characteristic of the drug/gene delivery scaffold;
determining a functional characteristic of a tissue to be implanted with the drug/gene delivery scaffold;
creating a first set of databases representing a plurality of microstructure designs for the drug/gene delivery scaffold in image-based format;
for each of the plurality of microstructure designs, calculating a drug/gene delivery profile of a resultant scaffold incorporating the microstructure design;
selecting a desired microstructure design for the drug/gene delivery scaffold, said selecting step including:
selecting the microstructure design that yields the resultant scaffold with the drug/gene delivery profile most closely matching the desired dosage level desired for tissue regeneration or tumor destruction, and the functional characteristic of the tissue to be implanted with the scaffold while satisfying the constraint on the functional characteristic;
creating a second database representing a desired geometry for the drug/gene delivery scaffold in imaged-based format; and
merging the databases representing the desired microstructure design with the second database to yield an image-based design of the scaffold.

34. The method of claim 33 further comprising converting the image-based design to a fabrication geometry.

35. The method of claim 33 wherein said desired functional characteristic of the drug/gene delivery scaffold further comprises at least one of release kinetics, concentration, drug half life, drug diffusivity in tissue, and drug advection.

36. The method of claim 33 wherein said constraint on the drug/gene delivery scaffold further comprises a minimum threshold to promote drug efficacy.

37. The method of claim 33 wherein said functional characteristic of the native tissue further comprises at least one of permeability and mechanical structure.

38. The method of claim 33 wherein said step of calculating the drug/gene delivery profile for a plurality of microstructure designs further comprises calculating scaffold degradation rate, mechanical environment within the scaffold, and scaffold permeability.

39. The method of claim 33 wherein said step of calculating the drug/gene delivery profile further comprises calculating the profile for a plurality of microstructure designs based on functional characteristics of structural designs.

40. The method of claim 33 wherein said step of calculating the drug/gene delivery profile for a plurality of microstructure designs further comprises calculating advection of a drug species to be delivered by the scaffold due to a mechanical environment within the scaffold and in tissue.

41. The method of claim 33 wherein said step of selecting the desired microstructure design further comprises identifying from the plurality of designs a set of designs that minimally satisfies the constraint on the functional characteristic of the drug/gene delivery scaffold.

42. The method of claim 33 wherein said step of calculating a drug/gene delivery profile of a resultant scaffold incorporating the microstructure design further comprises:
applying representative volume element theory to each of the plurality of microstructure designs.

43. The method of claim 33 wherein the desired shape of the scaffold matches a site to be implanted with the scaffold.

44. A method of generating a scaffold design comprising:
creating a first database representing a desired scaffold design in image-based format;
obtaining a second database representing a three dimensional area to be implanted with the scaffold in image-based format; and
merging the first database with the second database to yield the scaffold design.

45. The method of claim 44 wherein said first and second databases are created in an image based format.

46. The method of claim 45 wherein said second database is generated by an image scanning technique.

47. A method of generating a scaffold design comprising:
creating a first database representing a desired scaffold design in image-based format;
obtaining a second database representing a three dimensional area to be implanted with the scaffold in image-based format; and
merging the first database with the second database to yield the scaffold design;
wherein said first and second databases are created in an image-based format; said second database is generated by an image scanning technique; and
said merging step further comprises a Boolean operation.

* * * * *